US006884060B2

(12) United States Patent
Tanner et al.

(10) Patent No.: US 6,884,060 B2
(45) Date of Patent: Apr. 26, 2005

(54) APPARATUS FOR MANUFACTURING ENCAPSULATED PRODUCTS

(75) Inventors: Keith Tanner, Safety Harbor, FL (US); Steve Burnett, Clearwater, FL (US); David Walker, Bath (GB); Peter Beke, Tarpon Springs, FL (US); Norman Stroud, Safety Harbor, FL (US); Mani Sundararajan, Wilmington, DE (US)

(73) Assignee: R.P. Scherer Technologies, Inc., Las Vegas, NV (US)

( * ) Notice: Subject to any disclaimer, the term of this patent is extended or adjusted under 35 U.S.C. 154(b) by 0 days.

(21) Appl. No.: 10/016,352

(22) Filed: Nov. 2, 2001

(65) Prior Publication Data

US 2003/0085487 A1 May 8, 2003

(51) Int. Cl.[7] ............................................... B29C 47/14
(52) U.S. Cl. .................... 425/224; 425/377; 425/378.1; 425/447; 425/449
(58) Field of Search ............................. 425/224, 325, 425/377, 378.1, 378.2, 447, 449

(56) References Cited

U.S. PATENT DOCUMENTS

| | | | |
|---|---|---|---|
| 1,970,396 A | | 8/1934 | Scherer |
| 2,288,327 A | | 6/1942 | Scherer |
| 2,774,988 A | | 12/1956 | Stirn |
| 2,775,257 A | | 12/1956 | Stirn et al. .................... 137/341 |
| 3,005,233 A | * | 10/1961 | Upton et al. ............. 425/378.2 |
| 3,010,147 A | * | 11/1961 | Davies et al. ............ 425/382.2 |
| 3,423,493 A | * | 1/1969 | Klenk et al. ............. 425/378.1 |
| 3,680,997 A | * | 8/1972 | Dukert et al. ................ 425/381 |
| 4,028,024 A | | 6/1977 | Moreland ................. 425/133.1 |
| 4,289,718 A | * | 9/1981 | Vollbrecht et al. ............ 264/50 |
| 4,631,016 A | * | 12/1986 | Hay, II ........................ 425/224 |
| 4,817,367 A | | 4/1989 | Ishikawa et al. ............... 53/454 |
| 4,919,308 A | * | 4/1990 | Majkrzak .................. 222/146.5 |
| 4,940,499 A | | 7/1990 | Lebrun et al. ................. 156/69 |
| 5,146,730 A | | 9/1992 | Sadek et al. .................. 53/454 |
| 5,246,635 A | | 9/1993 | Ratko et al. ..................... 264/4 |
| 5,520,958 A | * | 5/1996 | Doesburg et al. ............ 427/316 |
| 5,523,537 A | * | 6/1996 | Johannes et al. ............ 219/421 |
| 5,645,639 A | * | 7/1997 | Doesburg et al. .............. 118/60 |
| 5,660,922 A | * | 8/1997 | Herridge et al. ............. 428/214 |
| 5,735,105 A | | 4/1998 | Stroud et al. .................. 53/411 |
| 5,740,660 A | | 4/1998 | Rowe ........................... 53/454 |
| 5,761,886 A | | 6/1998 | Parkhideh ...................... 53/454 |
| 5,833,904 A | * | 11/1998 | Muskalla et al. ............ 425/224 |
| 6,022,499 A | | 2/2000 | Schurig et al. .................. 264/4 |
| 6,217,902 B1 | | 4/2001 | Tanner et al. ................ 424/456 |

FOREIGN PATENT DOCUMENTS

| | | |
|---|---|---|
| WO | WO 94/13249 | 6/1994 |
| WO | WO 01/03677 | 1/2001 |

OTHER PUBLICATIONS

"The Theory and Practice of Industrial Pharmacy" (Lachman, Alieberman and Kanig), 3d. edition, published by Lee & Febiger, 1986, pp. 1–2.

Softgel (Soft Gelatin Capsule) Update, Robert F. Jimerson, Reprinted from *Drug Development and Industrial Pharmacy* (Interphex '86 Conference) vol. 12, No. 8 & 9, 1986, pp. 1–5.

\* cited by examiner

*Primary Examiner*—Robert Davis
*Assistant Examiner*—Joseph S. Del Sole
(74) *Attorney, Agent, or Firm*—Donald O. Nickey; Andrew G. Rozycki

(57) ABSTRACT

This invention relates to a method and apparatus for forming soft capsules and provides novel processing flexibility. The apparatus includes extrusion dies as an alternative to spreader boxes and the use of melt-on-demand technology to enhance the long term stability of the film-forming materials. Preferred embodiments provide a positive displacement pump to transport the molten film-forming material from the melt-on-demand device to the extrusion device and preferably a reservoir means disposed between said extrusion device and said means to melt said film-forming material. The encapsulation apparatus may also include a valved injection wedge.

18 Claims, 15 Drawing Sheets

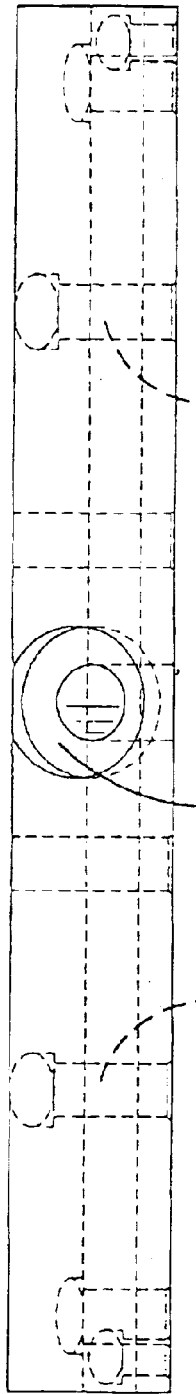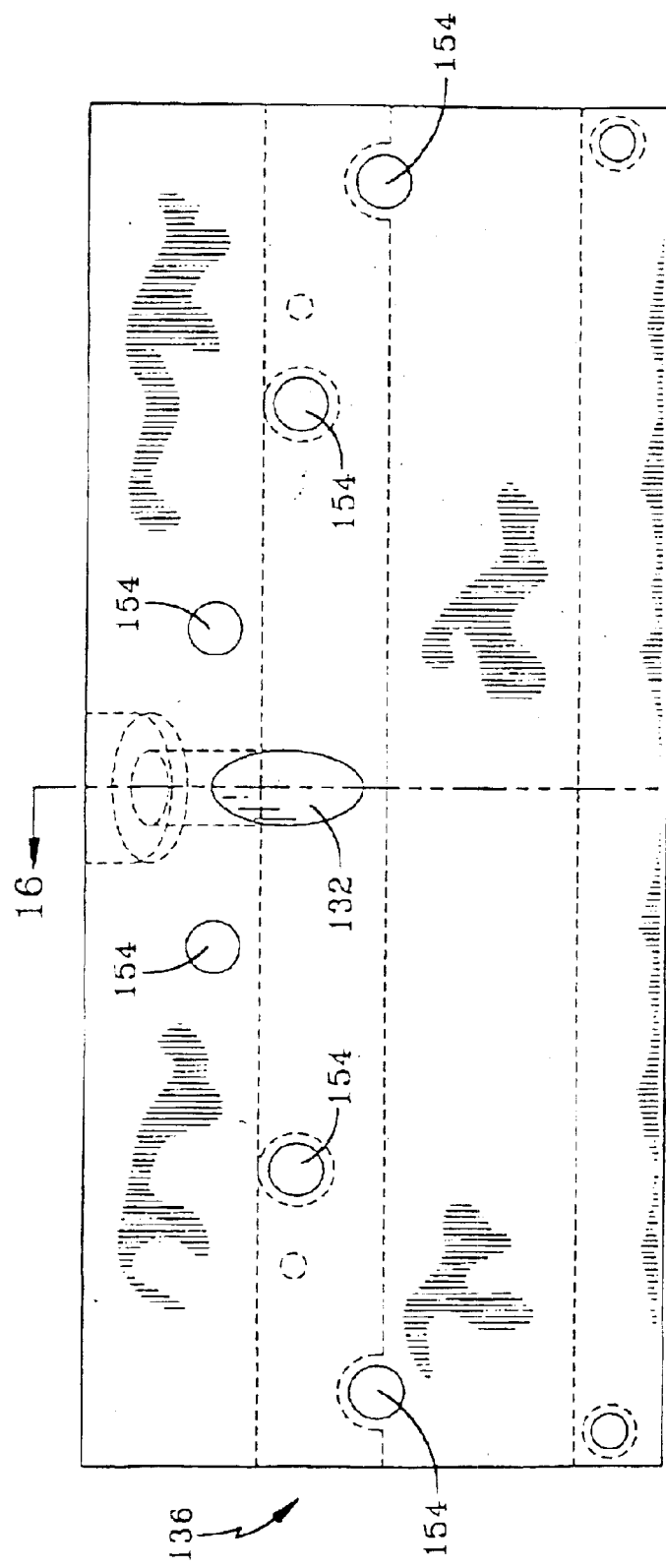

US 6,884,060 B2

APPARATUS FOR MANUFACTURING ENCAPSULATED PRODUCTS

TECHNICAL FIELD

This invention relates to an improved apparatus and method for producing encapsulated products, such as soft capsules filled with a liquid, suspension, solids, semi-solids, powders, tablets, medicines, nutrients and other materials. More specifically, the invention is directed to the use of melt-on-demand devices and extrusion dies to produce a ribbon of encapsulating film. The improved apparatus may also comprise a novel injection wedge.

BACKGROUND OF THE INVENTION

U.S. Pat. No. 1,970,396 to R. P. Scherer describes an early method and machine for producing soft gelatin capsules in an automated process. The process involves the formation of two gelatin sheets or films through the use of a gravity fed spreader box, cooling the liquid gelatin on two separate webs, then lubricating and guiding the two sheets into communication with each other between two co-acting dies while simultaneously dispensing the proper amount of medicine or other filling material between the sheets in registration with half cavities in the outer surface of the dies.

U.S. Pat. No. 4,817,367 to Ishikawa et al. introduced some improvements to the basic machine to aid in the set up, operation and quality of the capsules produced, however, a gravity fed spreader box was still used to form the gelatin ribbons or sheets.

U.S. Pat. No. 5,761,886 to Parkhideh discloses an apparatus for forming capsules that provides rotary dies that are independently moveable and the ability to vary the speed of the dies during the formation of a single capsule. The Parkhideh device also utilizes independently controlled casting drums to reduce "set-up" time and provide better quality control. Even though Parkhideh discloses a very sophisticated encapsulation machine, it still utilizes a gravity fed spreader box for formation of the encapsulating ribbon. Other patents relating to encapsulation techniques which disclose the use of spreader boxes to create the film or ribbon on a casting drum include U.S. Pat. No. 5,246,638 to Ratko et al.; U.S. Pat. No. 5,735,105 to Stroud et al.; U.S. Pat. No. 2,774,988 to Stim et al.; U.S. Pat. No. 6,022,499 to Schurig et al.; and U.S. Pat. No. 2,288,327 to Scherer.

One interesting reference is U.S. Pat. No. 4,028,024 to Moreland. It discloses a process and apparatus that prepares a gelatin encased medicament. The gelatin and the active are co-extruded as a column. This column is then pinched off by a pair of rotating wheels, each having half cavities therein to form capsules.

These previously utilized machines have many structural and operational shortcomings. Many of the shortcomings relate to the "set-up" of the machine. For example, the die to die timing, pump timing, ribbon formation and wedge adjustments are all important in protecting the equipment and providing a quality product. One aspect of the present invention resides in the use of a melt-on-demand extrusion technology and/or a valved wedge to decrease set-up time, reduce costs and improve product quality. The apparatus and process of the present invention allows for the use of encapsulating materials that were previously unusable on a standard rotary die encapsulation machine due to high viscosities or processing temperatures.

A general discussion of the basic technology, apparatuses and processes relating to the preparation of soft capsules is described in *The Theory and Practice of Industrial Pharmacy* (Lachman, Liberman and Kanig) $3^{rd}$ edition, published by Lee & Febiger.

Conventional technology for the manufacture of soft capsules using the rotary die process typically utilizes a spreader box metering system to cast the films or sheets onto a chilled surface, i.e., the casting drum. In one aspect of the present invention differs from conventional technology in the method of producing the sheets, ribbons or films. In the inventive process, extrusion dies are used as an alternative to spreader boxes. Further, the film-forming composition is not kept molten but rather is allowed to solidify and only the amount needed is melted just prior to its placement on the casting drum. In addition, the novel valved wedge according to the invention provides quick and economical set-up of the encapsulation machine.

The conventional process of producing gelatin films comprises mixing gelatin, plasticizers and water, and heating the mixture while stirring under vacuum. This results in a molten homogenous mixture that is referred to as a gelatin melt. This occurs at approximately 45–65° C. The molten system is drained into heated tanks that maintain the gelatin in a molten state during staging and casting of the films. Staging can be as long as two to three days. Before encapsulation, other additives such as colorants, preservatives, sweeteners, flavors, texture modifiers and the like may be blended into the melt.

During the prior art encapsulation process, the molten gelatin melt is transferred to the metering devices (spreader boxes) which are used to cast ribbons with a required thickness onto the casting drum. Commonly, the metering device consists of a heated reservoir that uses a gate box (a heated chamber or box with the rear portion fitted with a variable height slot) wherein the material flows via gravity through the slot onto the rotating casting drum. Film thickness is determined primarily by the height of the slot. Item 8 in Parkhideh, U.S. Pat. No. 5,761,886, is a spreader box. A second type of metering device meters the melt onto the rotating casting drum using doctor blades. A rotating cylinder mounted adjacent to the doctor blade assists with the flow of the gelatin. Ribbon thickness is determined by a) the gap between the doctor blade and the casting drum surface; and b) the speed of the spreader box cylinder. The cast ribbon solidifies onto the rotating casting drum after leaving the spreader box and this can take up to 10 to 15 seconds to achieve. The prior art spreader boxes are vented to the atmosphere and are not capable or designed to support pressure to facilitate the casting process.

U.S. Pat. No. 2,775,257 to Stim et al. discusses some of the shortcomings associated with the prior art film casting machines. This reference describes the use of casting hoppers where it has been found that the surface of the gelatin composition exposed to the air lost moisture by evaporation and formed a comparatively hard, inflexible scum or skin. Additionally, changes in the gelatin composition introduced by the evaporation of moisture from the surface caused undesirable variations in the film. Stim et al. found that by placing a layer of an inert liquid, such as mineral oil, on the surface of the melt, evaporation from the hoppers was prevented. This reference also provides a fairly good description of the use of a casting hopper or spreader box to form the ribbons.

In the prior art process, transfer of molten gelatin or melt from the holding tank to the metering device (or spreader box) is achieved in one of two ways. A common method is to suspend or mount the tank of molten gelatin above the encapsulation machine and allow the molten material to gravity fed through heated tubes into the reservoir of the metering device. Another transfer method conventionally used is to pump the melt via heated tubes from floor mounted staging tanks using either a peristaltic or lobe pump system. One requirement of the pump fed system is that the pump casing/components and in-line connections must be maintained above the melting point of the film-forming composition. If there are cold areas within the path, the material will freeze and prevent flow. In addition, both gravity and pump systems require a method of controlling flow to prevent overfilling of the spreader boxes.

The conventional process also relies on maintaining the film forming composition in a molten state from initial manufacture to just before encapsulation. Tanks used to feed the encapsulation machine require the entire tank to be maintained above the melt temperature of the film-forming composition. Prolonged maintenance of gelatin or other film-forming compositions in a molten state leads to degradation of the polymer, rendering the composition, after prolonged staging, ineffective at fabricating capsules. Gelatin melts can be staged typically no longer than 96 hours before unacceptable degradation occurs.

Gelatin melts can be cooled and allowed to solidify within the staging tanks to prevent degradation if prolonged staging is required. However, the major drawback is that the entire tank contents have to be remelted. This requires 8 to 15 hours of gently heating the material to raise the temperature of the gelatin mass to the required 60° C. Rapid heating of the system leads to localized heating, which can cause degradation and charring of the composition. Therefore, when stopping the encapsulation machine, a decision has to be made to: 1) continue to heat the gelatin which subjects it to degradation; or 2) allow it to solidify. The solidification subsequently requires the remelting which is very time consuming and expensive. Often, the result of stopping the encapsulation machine is that the melt is discarded which represents a significant waste of resources. Thermal degradation is often exacerbated by the addition of additives and can significantly shorten the available staging time.

Another drawback of the conventional process and apparatus is that it requires relatively low viscosities of the film-forming compositions. Spreader boxes rely on viscosities sufficiently low to enable the material to flow from the exit slot. The use of doctor blades and a rotating cylinder will enable slightly higher viscosity materials to be cast into films, but there is still a limit of about 20,000 to 25,000 cps on these metering systems. The conventional equipment and methodology therefore precludes the use of high viscosity film-forming compositions. Most alternative polymer compositions for forming films have viscosities significantly higher than that of gelatin.

An example of a film-forming composition that is not gelatin based is disclosed in International Application No. PCT/US00/18420, entitled: FILM-FORMING COMPOSITIONS COMPRISING MODIFIED STARCHES AND IOTA-CARRAGEENAN AND METHODS FOR MANUFACTURING SOFT CAPSULES USING SAME. In general, this application discloses an edible, soft capsule which comprises a soft, dry shell which comprises i) about 12–24 weight % iota-carrageenan; ii) about 30–60 weight % modified starch; iii) about 10–60 weight % plasticizer; and iv) about 1–4 weight % sodium phosphate dibasic buffer system. The viscosity of these compositions can range from 10,000 to above 30,000 cps and have proven to be difficult to utilize on the conventional encapsulation machinery. One aspect of the present invention resides in the discovery that these gelatin free compositions can be effectively utilized in the encapsulation system disclosed herein.

A further limitation of conventional equipment and methodologies is that it is extremely difficult to use a spreader box to form laminated ribbons. Laminated ribbons are ribbons that are cast one on top of the other. Laminated ribbons are sometimes desirable to modify the functional properties of the film, i.e., modifying the drying characteristics or retaining fill materials that are incompatible with standard encapsulation polymers. Through the use of the inventive melt-on-demand extrusion apparatus of the present invention, laminated ribbons are easily produced.

SUMMARY OF THE INVENTION

There is disclosed an apparatus for preparing films suitable for encapsulation from a solid film-forming material comprising:

a) at least one casting drum;

b) means for melting said film-forming material on demand;

c) pump means; and d) an extrusion device.

The inventive encapsulation apparatus uses a conventional casting drum known to those skilled in the art upon which to extrude the film forming material. These drums can vary in size and may be air or liquid cooled. Typically, these casting drums are stainless steel or chromed iron.

One aspect of the present process and apparatus is that the film-forming materials are prepared in bulk and allowed to solidify. The material can be cast into blocks or bricks, or placed in 55 gallon drums. Thus, the film-forming material can be stored for long periods of time without fear of degradation. Another aspect of the present apparatus and process is that the solid film forming material is melted on a continuous basis at a rate about equal to the rate of deposition/extrusion of the film onto the casting drum. Representative "melt-on-demand" devices are disclosed below. The melted material is then pumped under pressure to the extrusion device which preferably has an internal cavity in the shape of a coat hanger, to facilitate the even and consistent extrusion of the film.

The film-forming material or composition can be any material known in the art to be useful for encapsulation or enrobing technologies. Typically, these film-forming materials comprise at least one component selected from starch, gelatin, carrageenans, gums or synthetic materials such as hydroxypropylatedmethylcellulose (HPMC) and the like. The film-forming material typically has an aqueous base and is considered to be ingestible. As used herein, the term "ingestible" is used to indicate a film-forming material that dissolves under conditions simulating the human digestive tract or water.

One especially preferred film-forming material or composition that can be utilized in the apparatus and process of the present application, is a composition comprising iota-carrageenan and at least one modified starch selected from the group consisting of hydroxypropylated tapioca starch, hydroxypropylated maize starch, acid-thinned hydroxypropylated corn starch, native potato starch, hydroxypropylated potato starch, pre-gelatinized modified corn starches, and wherein said starch has a hydration temperature below about 90° C. and wherein the weight ratio of modified starch to iota-carrageenan ranges from 1.5:1 to about 4.0:1. This film-forming composition, when dried, consists essentially of from 42–84% by weight gel formers comprising a mixture of iota-carrageenan and modified starch; water; a plasticizer; and a buffer. In general, any hydroxypropylated vegetable starch would be useful in preparing the film-forming composition.

During the operation of the apparatus according to this invention, only that amount of film-forming material as is required is melted in the melt-on-demand device and transported under pressure to the casting drum. This apparatus for melting the film-forming material comprises a melt grid. The grid may be above the solid film-forming material or below the solid film-forming material. The apparatus and process according to the present invention also requires the presence of a positive displacement pump. This pump is used to transport the molten film-forming material from the melter to the extrusion device. These positive displacement pumps can be selected from the group consisting of gear pumps, lobe pumps, sine pumps, and archimedes screws.

Preferentially, the apparatus according to the invention additionally comprises a reservoir means disposed between said means to melt said film forming composition and said extrusion device. The extrusion device typically comprises a chamber and an extrusion slot. Preferably, the extrusion device is a "coat hanger" die. Even more preferred is an encapsulation apparatus that comprises a valved injection wedge.

There is also disclosed an apparatus for preparing soft capsules, the apparatus comprising at least one casting drum and an extrusion device wherein said casting drum has deposited upon it by said extrusion device, a ribbon of material useful for encapsulation; and wherein said extrusion device is tilted from 2 to 10° from perpendicular and away from the direction of flow from the extrusion device. Preferably, the tilt is about 5°.

The invention also relates to an apparatus for preparing an ingestible film, said apparatus comprising:
 a) at least one casting drum;
 b) means to melt a solid ingestible film forming composition on demand;
 c) pump means to transport the molten composition to an extrusion device; and
 d) reservoir means disposed between said means to melt said composition and said extrusion device.

There is further disclosed an apparatus for applying a polymer to a substrate comprising:
 a) means to melt said polymer on demand;
 b) pump means to transport the molten polymer to an extrusion device;
 c) reservoir means disposed between said means to melt said solid polymer and said extrusion device; and
 d) at least one casting drum.

The reservoir means is essentially a small tank that contains an amount of the molten composition sufficient to allow for the change out of the melt-on-demand device without stopping the encapsulation machine. In a more preferred embodiment, the apparatus additionally comprises a distribution manifold disposed between said reservoir and said extrusion device.

The present invention also relates to a process for the preparation of films suitable for encapsulation comprising the steps of:
 a) preparing a liquid gel mass;
 b) solidifying said liquid gel mass;
 c) melting only a portion of said solid gel mass as required and pumping the molten gel mass to an extrusion device; and
 d) forcing the molten gel mass through said extrusion device.

There is further disclosed an apparatus for forming capsules comprising:
 a) a plurality of movable dies cooperatively forming an encapsulation region;
 b) means for holding and pumping an active fill material;
 c) means for holding and pumping a placebo fill material; and
 d) a valve disposed between said encapsulation region and said means for holding and pumping fill material, adapted to switch between the placebo fill material and the active fill material.

BRIEF DESCRIPTION OF THE DRAWINGS

FIG. 14 is a top plan view of the front plate of an extrusion device according to one embodiment of the invention.

FIG. 15 is a side plan view of the front plate of an extrusion device according to one embodiment of the invention.

DETAILED DESCRIPTION OF THE PREFERRED EMBODIMENTS

Figure 1:
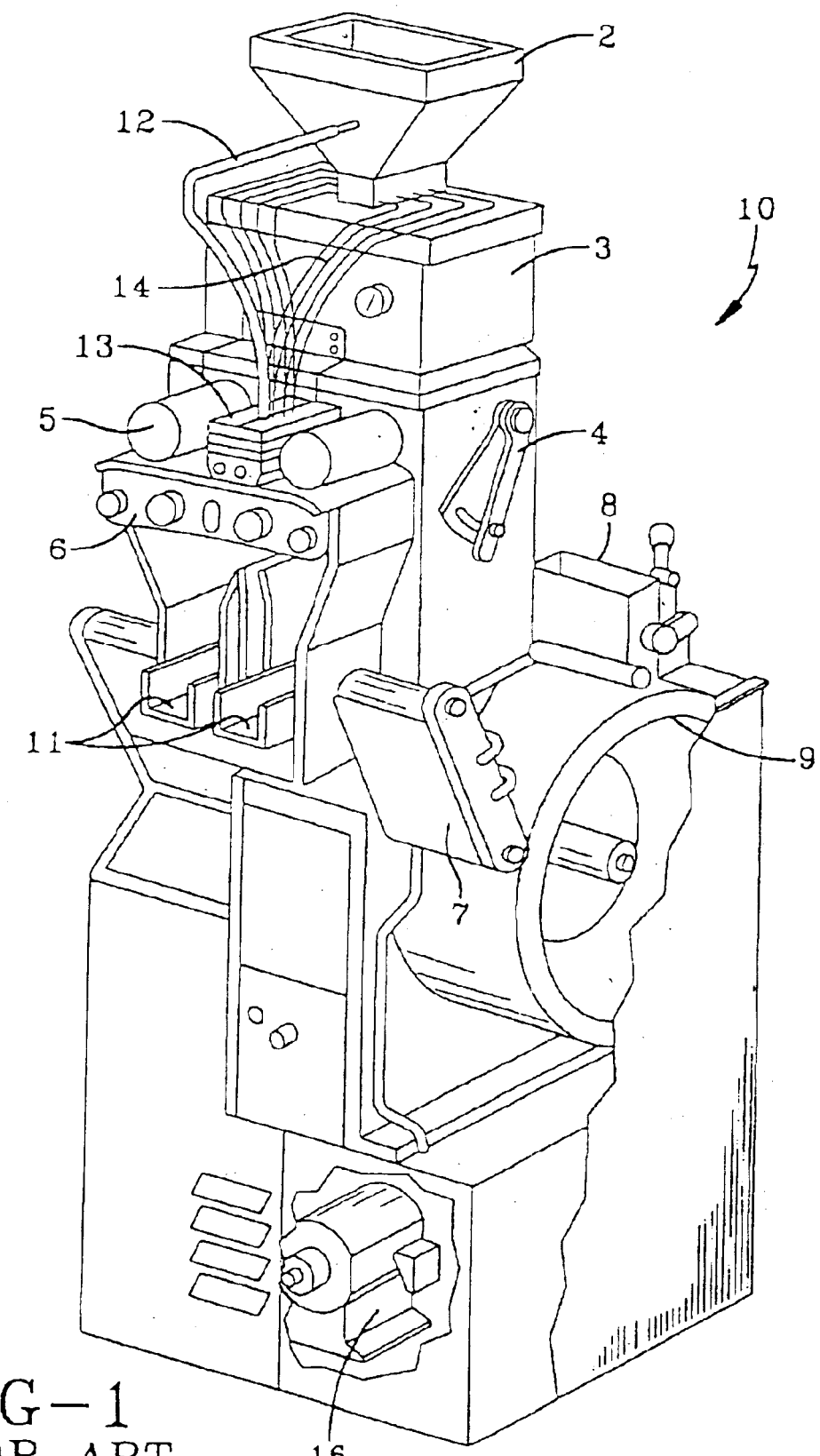
FIG. 1 is a front perspective view of a representative prior art machine, partially cut away.

FIG. 1 shows a front perspective view of a typical prior art soft capsule machine 10. The motor 16 that operates the machine is shown in the cutaway view of the base. The casting drum 9 on the right side is shown under the cutaway portion of the skin. The fill hopper 2 is shown above the pump and pump housing 3. Element 4 is the pump lifting handle. The gelatin ribbon (not shown) starts out as liquid in spreader box 8 which maintains the gelatin in a liquid state using heat. The spreader box 8 is typically gravity fed and places the gelatin melt on the casting drum 9 using conventional techniques. The casting drum 9 rotates and results in the formation of a continuous sheet or ribbon of gelatin. Cooling the molten gelatin on the casting drum creates a flexible gelatin ribbon which is threaded through oil roller assembly 7. An edible lubricant is typically placed on both sides of the ribbon to assist in the transfer of the ribbon to the rotary dies (not shown). In this machine, the ribbon makes a twist to enable it to be passed over ribbon roller 5 and then to wedge 13. Two ribbons are formed in the same manner using identical assemblies on either side of the machine (not shown). The gelatin ribbon formed on one drum provides the shell material for one side of the capsule. The rotary dies are housed behind the yoke assembly 6. The gelatin ribbons are threaded over the co-acting dies (not shown) into communication with each other. Pressure is applied to the dies to force them against each other. This force, in conjunction with heat from the wedge assembly, causes the two ribbons of gelatin to be sealed together and cut along the cavities on the dies to produce a semiformed, empty capsule. In simultaneous action, pump assembly 3 measures and dispenses the fill material (i.e., nutritionals, pharmaceuticals and the like) through the tubes 14 into the injection wedge and then into the semi-formed, empty capsule via injection ports in the fill material distribution device or wedge. The rotation of the dies continues the sealing and cutting process to form a complete filled capsule. Output shoots 11 receive the completed capsules. During the set up and other non-production phases, the fill material is returned/recycled to the fill hopper 2 via return hose 12.

In contrast, the inventive apparatus replaces the spreader box 8 with a sanitary, coat hanger extrusion die. Further, the holding tank for molten gelatin is replaced with a melt-on-demand device. Lastly, the inventive apparatus would have two fill hoppers, one for placebo fill and one for active fill; two sets of fill lines 14 and two sets of return lines 12. The inventive apparatus would also have a valved injection wedge that would allow the rapid switching from an active fill to a placebo fill and vice versa.

Figure 5:
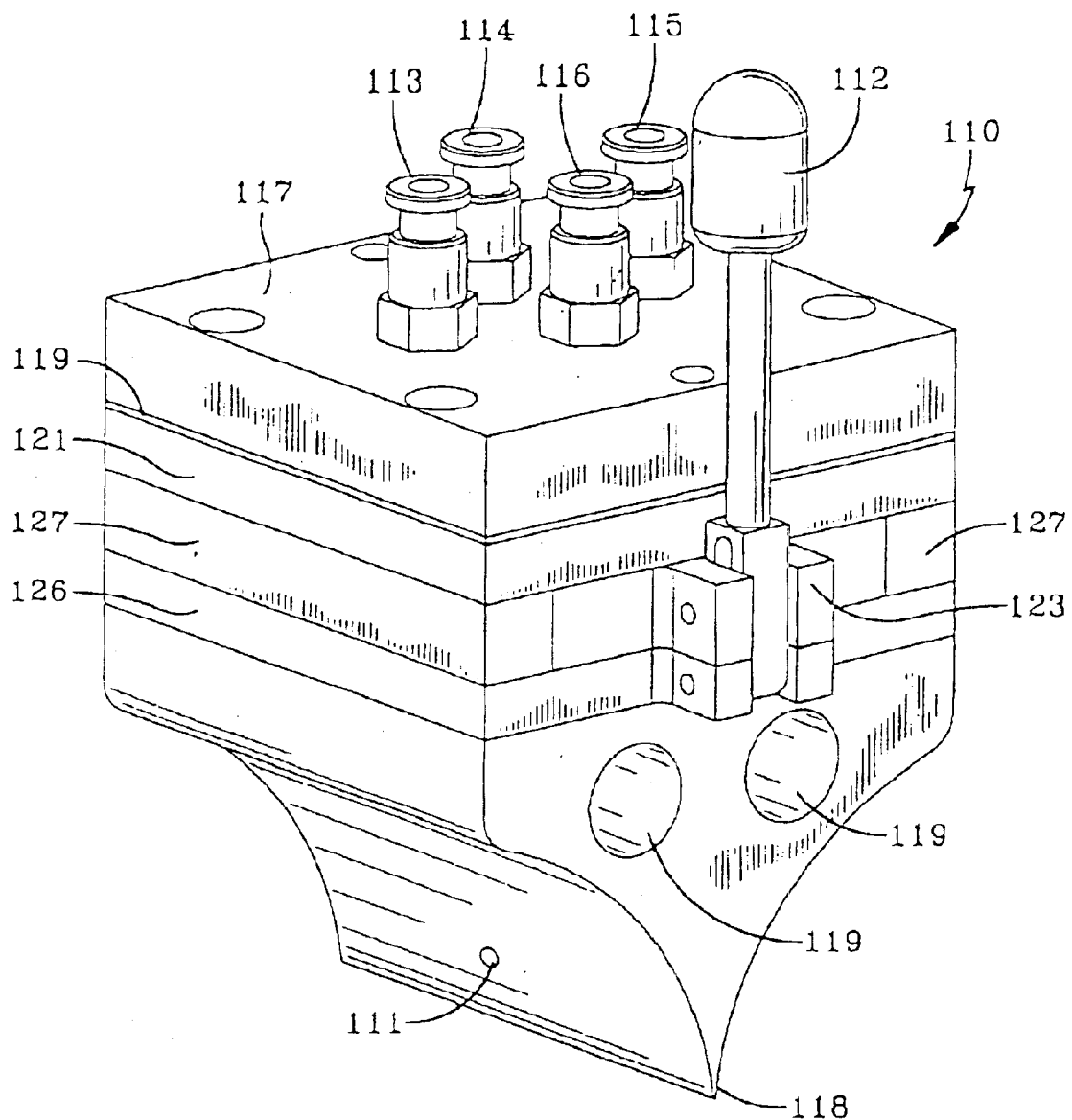
FIG. 5 is a perspective view of a fill material distribution device or injection wedge that comprises a valve for switching between an active fill and a placebo fill.
Figure 6:
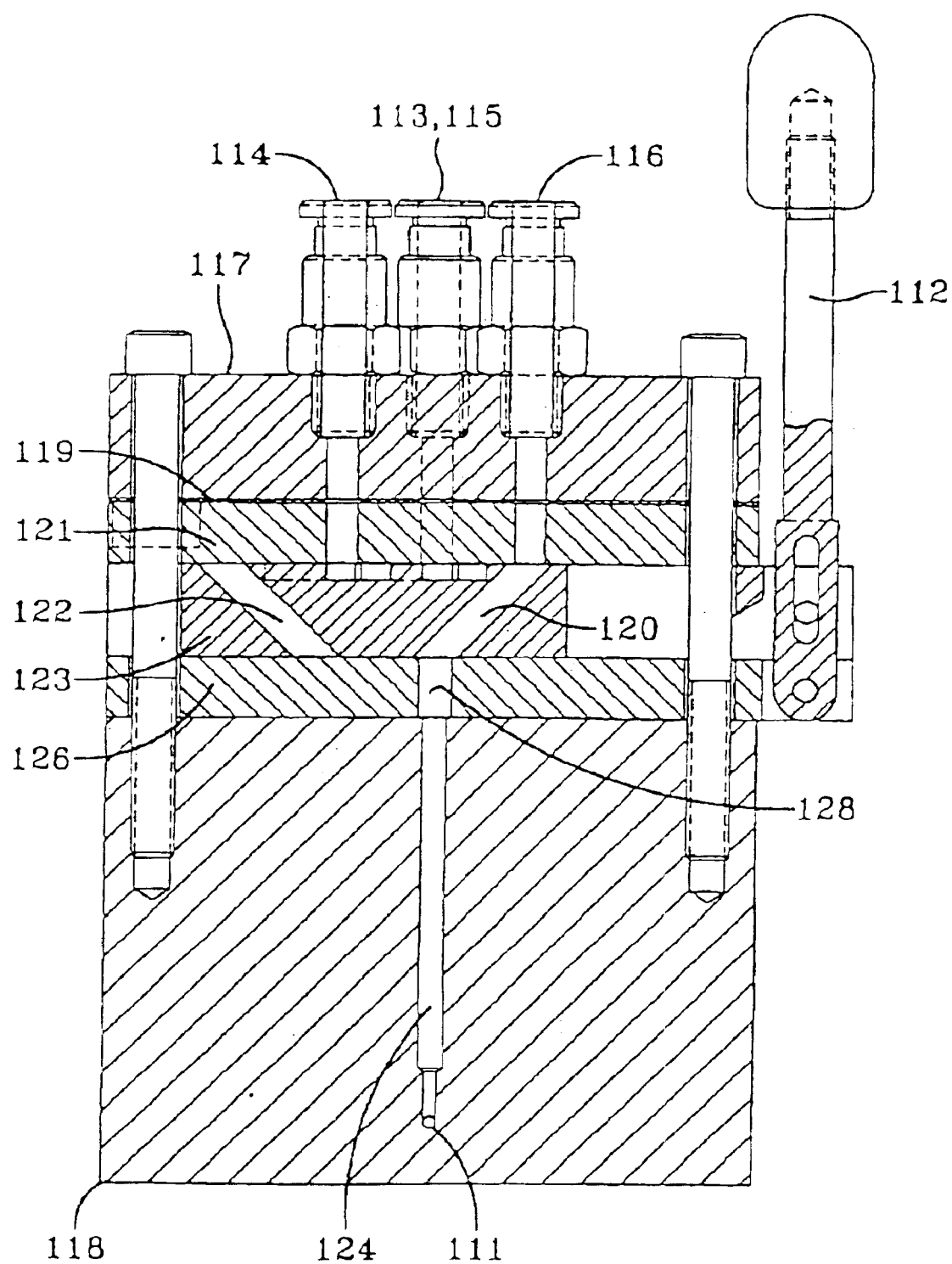
FIG. 6 is a fill material distribution device or valved injection wedge in cross section in the placebo fill position.
Figure 7:
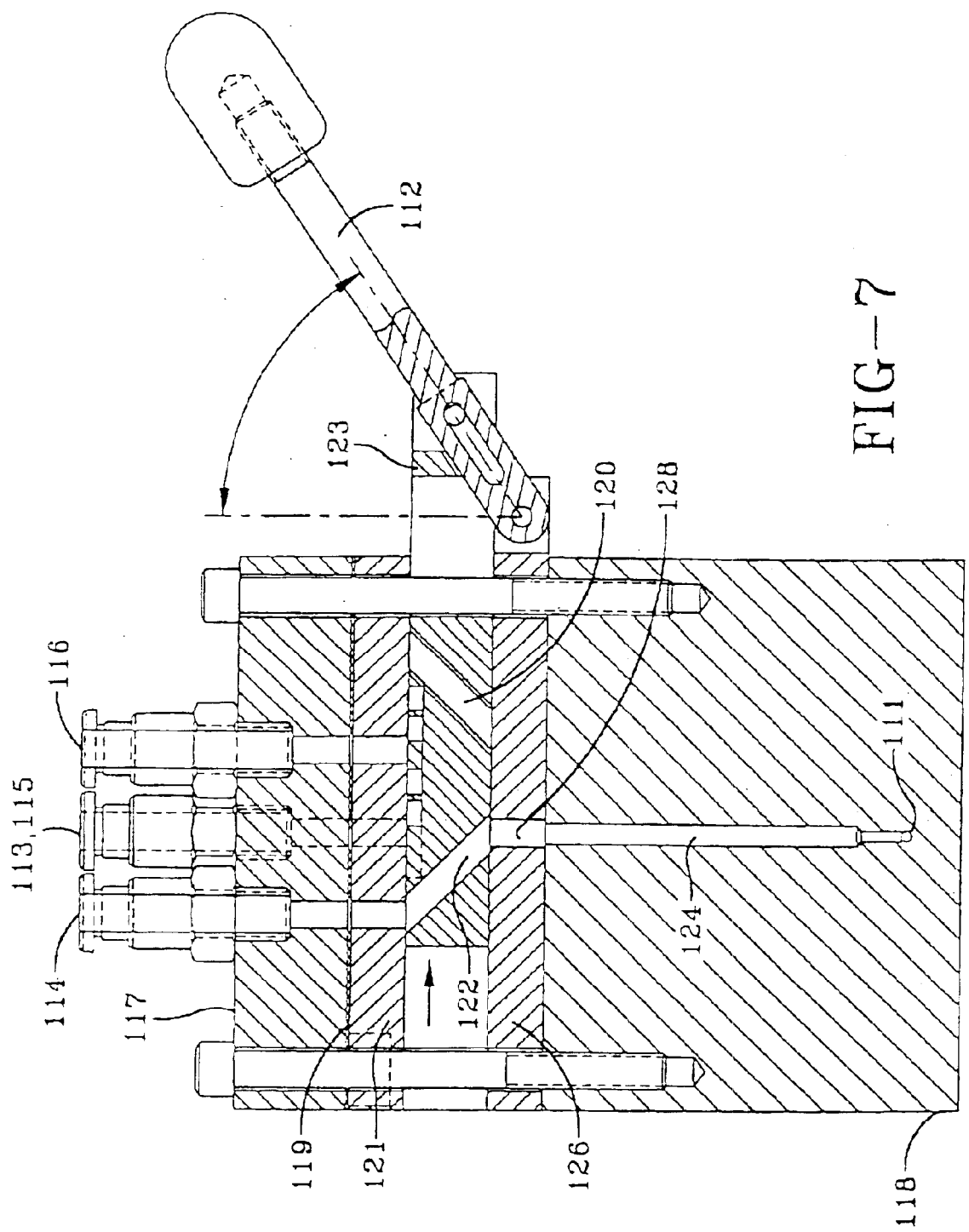
FIG. 7 is the fill material distribution device of FIG. 6 in the active fill position.

One embodiment of the present invention relates to the placement of a valve in the wedge injection as seen in FIGS. 5–7. When encapsulation machines are "set up", they typically run without injecting fill material. In the alternative, they are run using an active fill. The placement of a valve in the wedge provides the advantage that the machine can be set up with placebo and then quickly switched over to the active fill material. This has the advantage of being able to make soft capsules with very small amounts of raw material and conserve the active fill. In this embodiment, a second hopper and pump is utilized and filled with placebo fill material.

Figure 2:
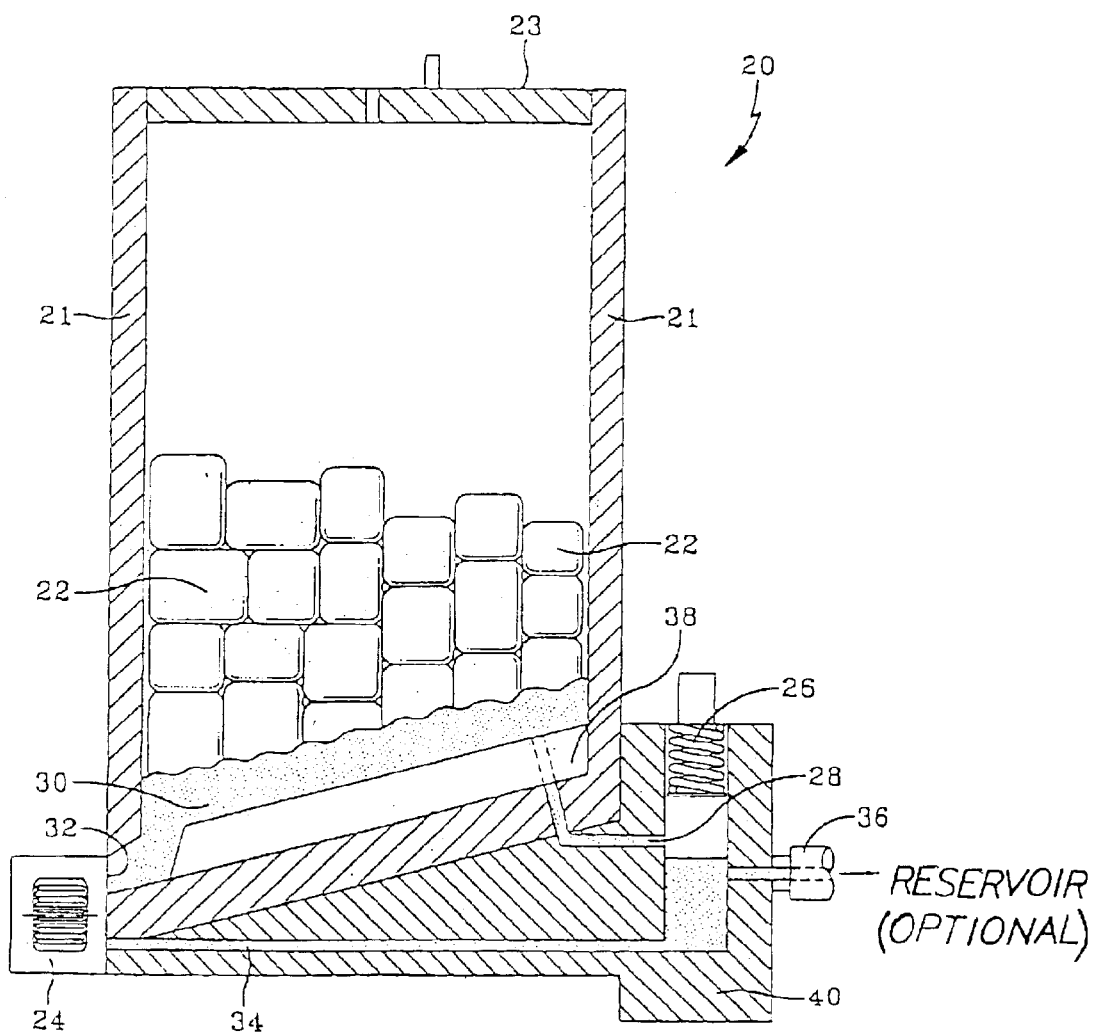
FIG. 2 is representative of a melt-on-demand device useful in the present invention, in cross section.

FIG. 2 is illustrative of one version of a melt-on-demand device useful in the present invention. The device 20 generally consists of insulated walls 21 and a melt grid 38. The solid film-forming composition is represented by blocks 22 inside the device 20. Access to the interior of the device 20 is through door 23. The solid film-forming material 22 rests upon the melt grid 38. This melt grid 38 is sloped slightly and provides an area of molten film-forming material 30 between the solid 22 and the melt grid 38. This molten material 30 enters through gateway 32 into gear pump 24. Gear pump 24 provides the necessary pressure for line 34 which is connected to a heated hose 36 that proceeds to the extrusion die. A pressure feedback line 28 and a pressure relief valve 26 are disposed within manifold block 40. The pressure relief valve 26 controls the amount of molten material 30 flowing through heated hose 36 to the extrusion die (not shown) or being recycled back through the melt grid 38 to the pool of molten material 30 between the solid film forming material 22 and the melt grid 38.

The gear pump 24 can be carefully controlled in conjunction with the pressure relief valve 26 to provide a steady and consistent supply of molten film-forming material to the extrusion die. Those skilled in the art will appreciate that controlling devices are commercially available for the pump and pressure relief valve that will provide the required, consistent pressure. In one embodiment, a reservoir is disposed between the pump of the melt-on-demand device 20 and the extrusion device (not shown).

Figure 3:
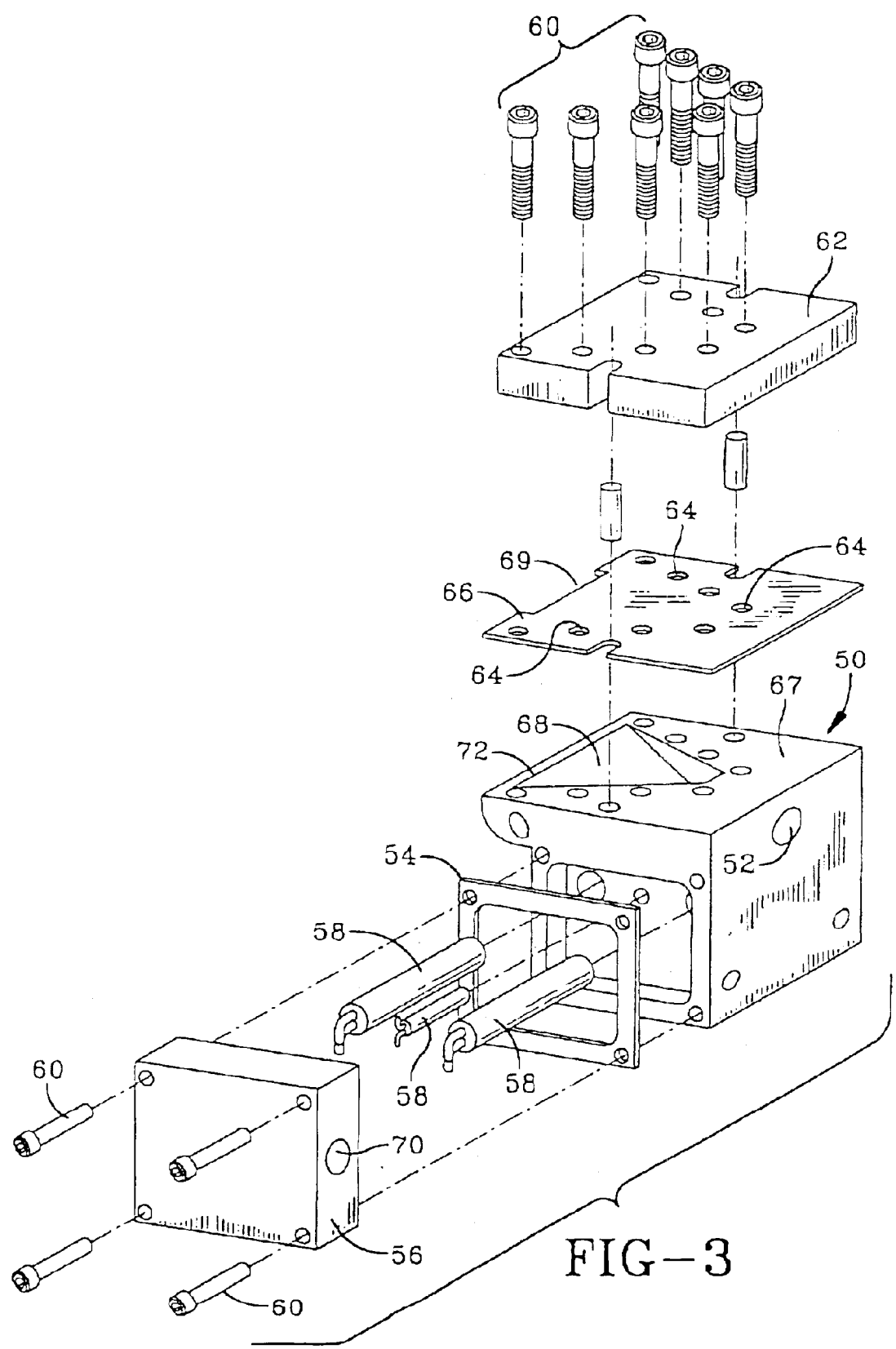
FIG. 3 is an extrusion device in accordance with an embodiment of the present invention in an exploded perspective view.

Referring now to FIG. 3, shown is one embodiment of the extrusion device in exploded perspective. The main body 50 contains the coat hanger type cavity 68 and lip 72. Entrance port 52 is where the molten film-forming material enters the extrusion device under a pressure of about 10–35 psi (about 70 to 245 kPa).

The front face of the main body 67 is in contact with a shim 66. The shim contains a cut out 69 and numerous holes 64 to accommodate bolts 60. The shim cut out 69 can be adjusted to alter the thickness of the ribbon. In an alternative embodiment, the shim may be eliminated and the front plate 62 may have an opening or cut out placed therein. Bolts 60 pass through the front plate 62, the shim and into the main body 50 of the extrusion device. On a side adjacent the front face 67 of the main body 50 are heating elements 58, end piece 56 and port 70 for electrical connections. A gasket 54 is disposed between the main body 50 and the end piece 56.

The heating elements 58 contained within the main body are carefully controlled by thermisters (not shown). Those skilled in the art will appreciate that controlling devices are commercially available for the heating elements that will provide the required constant pressure. The temperature of the film-forming material at the point of exit from the extrusion device is critical to extruding a high quality film. The inventors have also determined that the pressure at the lip 72 is critical in obtaining an acceptable ribbon. In addition, the height of the lip is important. The lip should preferably be of a height of from ½ to 1 inches (about 1 to 2.5 cm).

Further, the pressure differential across the face of the opening of the extrusion device should vary by no more than 2%. In general, the pressure of the film-forming composition in the extrusion device is about 10–12 psi (about 70 to about 85 kPa) at the entrance port 52. The coat hanger design can be varied depending upon the viscosity and temperature of the film-forming composition. What is important in designing the extrusion device is that laminar flow and laminar thickness occur across the entire opening or shim cut out 69 and down the lip 72 of the extrusion device. Through the application of even pressure at a given temperature, and the design of the coat hanger cavity 68, a wide variety of film-forming materials can be cast upon the casting drum to result in an acceptable encapsulation film.

Figure 4:
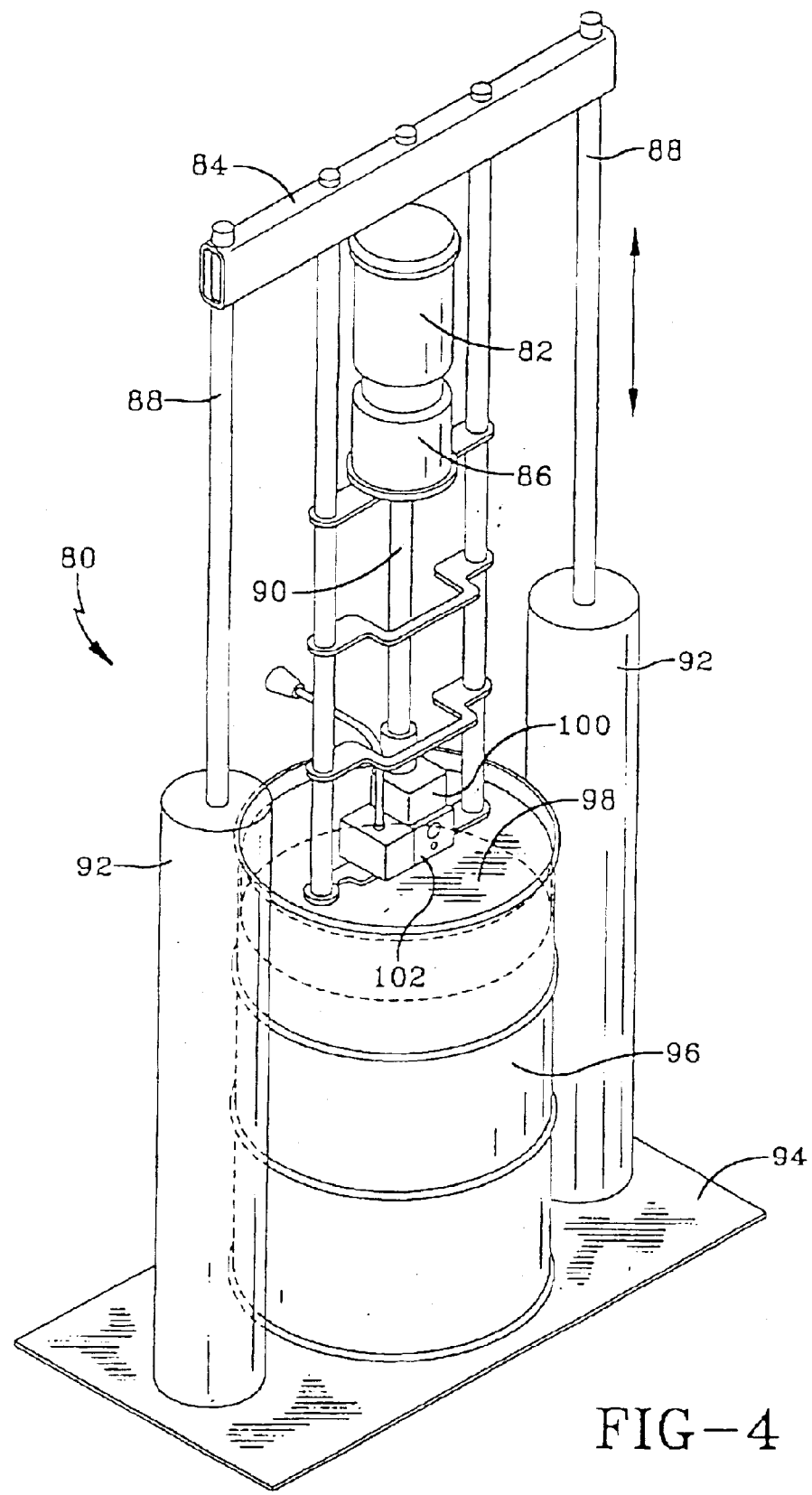
FIG. 4 is a representative melt-on-demand device in perspective view that is adapted for removing a solid film forming composition from a 55 gallon drum.

FIG. 4 is another melt-on-demand device that is more specifically known as a drum unloader 80. This particular device has the solid film-forming material 55 gallon drum 96. This drum sits upon a base 94. The melt-on-demand device 80 further comprises a motor 82, a gear box 86, connected to a shaft 90 which in turn is then connected to a pump 100 and a distribution manifold 102. A tie bar 84 communicates with pneumatic cylinders 92 and ties rods 88 to hay the entire unit move up and down in a vertical fashion. The platen or melt grid 98 is heated and melts the solid film-forming material in the drum 96 which is forced into the pump 100 cavity and out through the distribution manifold 102. Representative of such melt-on-demand devices are the Dynadrum 55 manufactured by ITW Dynatec of Hendersonville, Tenn.; Uniflow Product manufactured by Industrial Machine Manufacturing, Inc. of Richmond, Va.; and Robotech AG of Switzerland.

One feature of the melt-on-demand device represented in FIG. 4 is that the rate of flow from the distribution manifold is determined by the pump 100 and the pressure applied by the pneumatic cylinders 92.

This melt on demand device was originally developed for the application of hot melt adhesive glues to packaging and the like. Substantial modifications of these machines have been made to accommodate film-forming compositions which are useful in the production of soft capsules using the rotary die process. Modifications include protecting parts that contact the film-forming material to prevent corrosion and modifications to the melting platen 98 to obtain the flow required to the extrusion die. The platen or melt grid 98 are typically fabricated from aluminum, anodized and coated with polytetrafluoroethylene (Teflon®). The Teflon surface is used to reduce the frictional forces of solid, film-forming material moving towards the melt grid 98. This melt-on-demand device utilizes pneumatic rams 92 to push the heated platen 98 into a 55 gallon drum where the solid film-forming material is melted and removed by the gear pump 100. The distribution manifold 102 may have one or more hose units connected to it. These electrically heated hoses (not shown) preferably have one piece stainless steel hose fittings which eliminates cavities and thus prevents contamination. These heated hoses must be constructed so that they may be cleaned of the highly viscous film-forming material. Such hoses are available from Viking Industries, Inc. of New Smyrna Beach, Fla.

One important benefit of the melt-on-demand devices represented in FIGS. 2 and 4 is that they prevent charring of the film-forming material. As heat is applied to a film-forming material, the complex polymers break down and degrade and continue to do so as temperature and time increase. The prior art methodology and apparatus for maintaining the film-forming materials in a molten condition results in charring since oxygen is typically present. The present inventors have determined that by carefully controlling the heat applied to the solid film-forming material in the melton-demand devices, that charring can be greatly reduced and virtually eliminated through the exclusion of oxygen in the system.

The use of such melt-on-demand devices in the encapsulation industry is unique and provides tremendous advantages over the prior art methods and apparatuses. The system according to the present invention provides temperature stability in each melt zone, reduction of heat transfer from one zone to another, isolation of film-forming materials at high temperatures from oxygen, in a sanitary, easily cleanable device.

FIG. 5 is a perspective view and represents another aspect of the present invention that relates to a valved injection wedge, generally 110. The wedge in an encapsulation machine is the device that inserts the fill material in between the two films just prior to the nip of the two rotary dies completing the capsule. Injection wedges are typically heated to pretreat the films prior to capsule formation and contain a number of fill exit ports 111 at or next to the apex 118 of the wedge. The number of exit ports 111 will equal the number of rows of cavities in the rotary dies. The valved wedge 110 replaces the conventional wedge and shut-off valve as seen in U.S. Pat. No. 5,761,886 at elements 27 and 13 and item 26 in U.S. Pat. No. 6,022,499. The wedge according to the present invention differs from those of the prior art in that it allows the prompt switching from a placebo fill material to an active fill material and vice versa. This allows the machine to be set-up without wasting valuable active fill material. Typically, during the set-up of encapsulation machines, only some of the machine's settings can be made without using fill material. Complete machine set-up requires the use of fill material. The valved wedge according to the invention requires separate pumping and reservoir capability for the placebo and active fill materials.

Thus, in operation, the encapsulation machine operator can begin the set-up of the machine through the use of a placebo fill. This would be accomplished by having lever 112 in the placebo position. See FIG. 6. After accomplishing the proper set up of the encapsulation machine, the operator would move the lever 112 to the active position as seen in FIG. 7. An encapsulation apparatus with a valved injection wedge is especially useful for the manufacture of small quantities of soft capsules. This ability to switch from placebo to active fill is an advancement in the state of the art in terms of the amount of active material required to manufacture the soft capsules and the quality of the final product.

In essence, the valved injection wedge is a three-way valve for each injection port 111. While three way valves are well known, the novel aspect of this invention is its application to rotary die encapsulation processes.

Figure 5A:
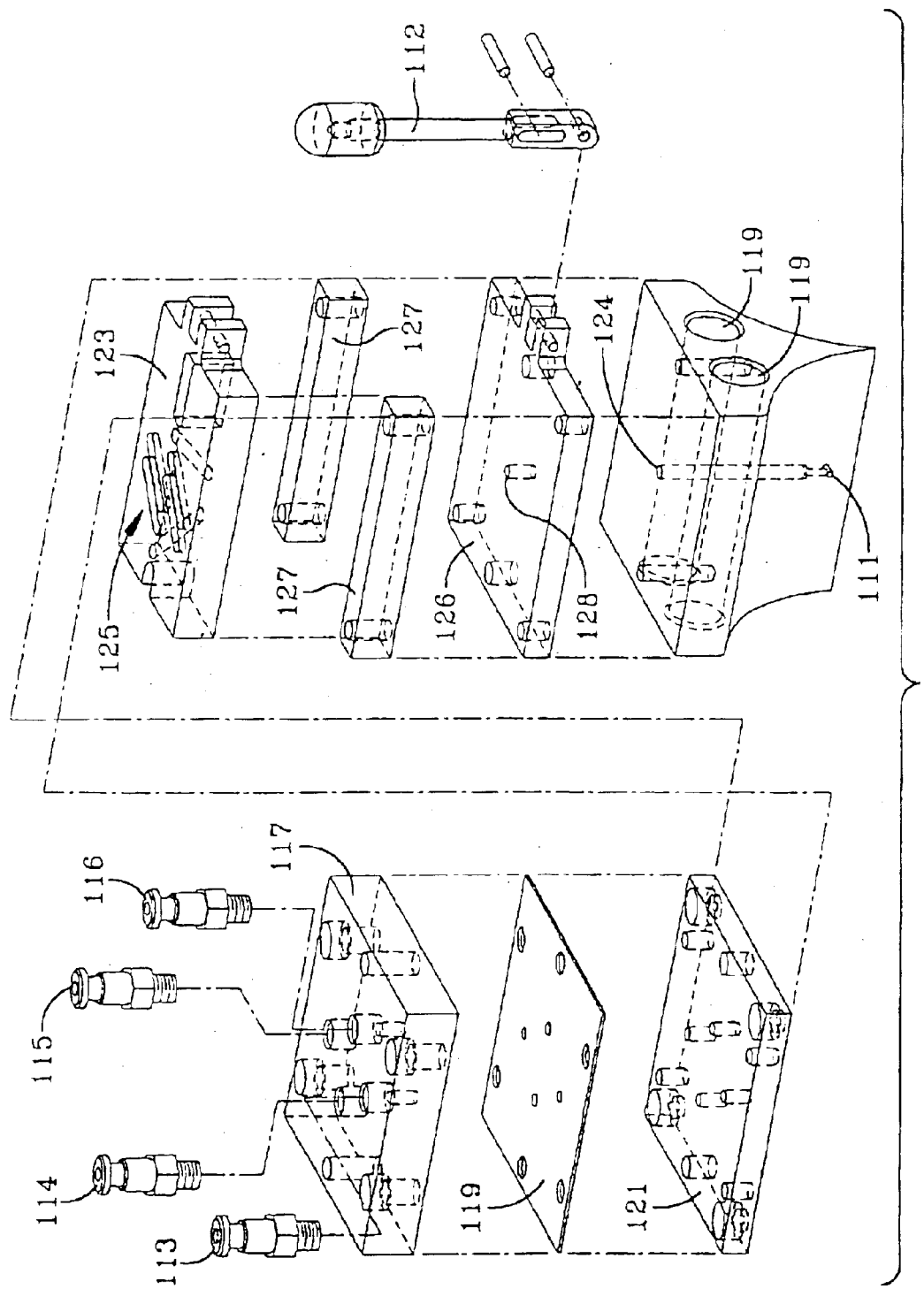
FIG. 5A is an exploded perspective view of an embodiment of the valved injection wedge according to the invention.

FIG. 5A represents an exploded perspective view of the valved injection wedge illustrated in FIG. 5. Those skilled in the art will appreciate that the valved injection wedge set forth in FIGS. 5, 5A, 6 and 7 would produce only one row of capsules as there is only one fill exit port 111. Commercial scale valved injection wedges would contain numerous fill exit ports, i.e., 5 to 15.

Referring to FIG. 5A, the representative valved injection wedge comprises return ports 113 and 115, injector ports 114 and 116, lead plate 117 and gasket 119. Below the gasket 199 is the upper guide plate 121. The upper guide plate 121 performs the function of a manifold. The distributor/shut-off plate 123 contains numerous channels 125 that directs the flow of active or placebo fill from injector ports 114 and 114 to exit port 111, back to return ports 113 and 115, or to a fully closed position (not shown). Blocks 127 hold the distributor/shut-off plate 123 in position and prevents lateral movement of plate 123. Lower guide plate 126 works in conjunction with upper guide plate 121 to physically support and act as manifolds for the moveable plate 123.

The channels 125 are configured such that at any position of level 112 (active fill, placebo fill or shut-off), both the active and placebo fills are never stagnant. When not being used as the fill material, they are recycled to the fill hopper 2. Those skilled in the art will appreciate that other designs of the valve can be used to accomplish the results set forth above.

Referring to FIGS. 5, 5A, 6 and 7, elements 113–116 are preferably quick star push-in fittings. Fitting 113 is the active return port; 114 is the active injector port; 115 is the placebo return port; and 116 is the placebo injector port. The valve is designed so that if active fill is selected, the placebo fill recirculates from the injector port 116, out the placebo return port 115 and back to the placebo fill reservoir (not shown). In similar fashion, when placebo is selected, active fill material recirculates. When neither active nor placebo are selected (the off position), both placebo and actives recirculate. Wedge apex 118 is positioned very near the nip of the dies. Elements 119 are openings for placement of heating elements.

In FIG. 6, the flow channel 120 of placebo fill through connector 128 is placed into channel 124 that exits near the apex 118 of the wedge through exit ports 111. The active flow line 122 through connector 128 is opened by moving the lever to the down position so that active injector 114 aligns with line 122, that aligns with line 124, which in turn aligns with exit ports 111. Element 111 is the exit port on each side of the wedge. For purposes of illustration, only one set of exit ports are shown. In commercial production, the number of pairs of exit ports 111 will equal the number of cavities across a face of the rotary die.

Figure 8:
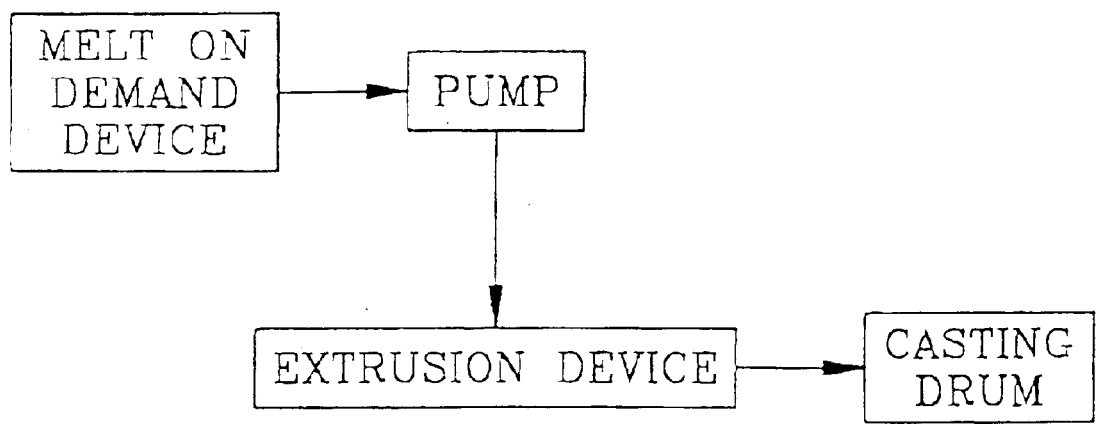
FIG. 8 is an apparatus flow diagram of the ribbon casting process according to the present invention.

FIG. 8 is an apparatus flow diagram of the method according to the present invention wherein each block represents an apparatus component. The essence of the present invention resides in the use of a melt-on-demand device in combination with a pump to supply an extrusion device that utilizes laminar flow technology to cast a high quality ribbon upon the casting drum. The ribbons produced using the apparatus and process described herein are very uniform in thickness with very few defects.

The present invention differs from the prior art in the aspects of staging the film-forming composition and the method of producing the ribbon on the casting drum. The film-forming composition may be those described in the prior art or using new compositions. In the present invention, the liquid, film-forming composition is placed within a container (i.e., a 55 gallon drum) or a reservoir of a melt-on-demand device and allowed to solidify.

Figure 13:
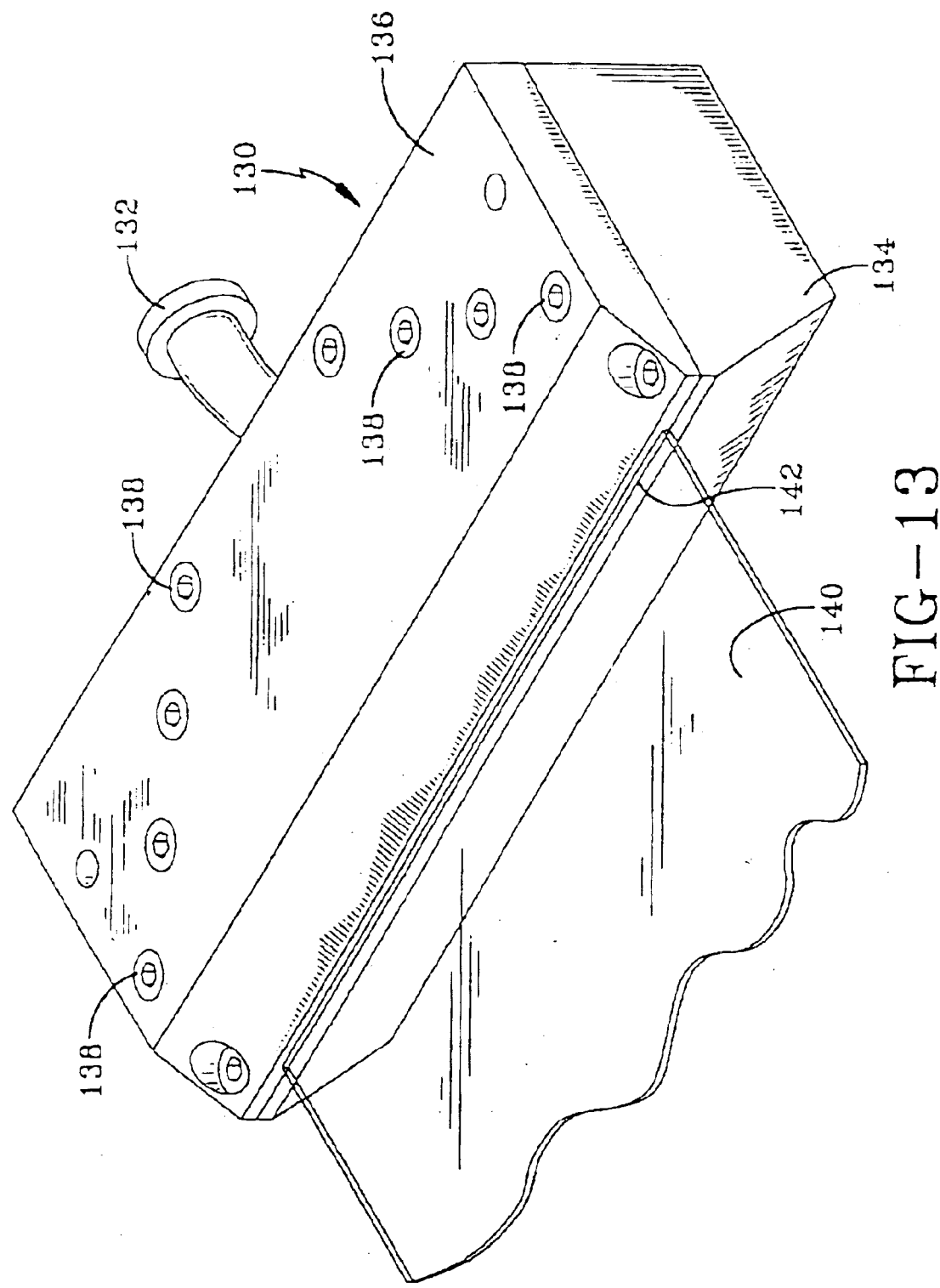
FIG. 13 is a perspective view of an assembled extrusion die useful in the present invention.

Further, the present invention is different from the prior art in that the spreader box is replaced with an extrusion die (See FIG. 13). The die is different from a spreader box in that the film-forming composition is pumped under pressure through a slot under laminar flow. The uniform thickness of the ribbon is also achieved through a design of the extrusion die that provides for equal pressure distribution across the die opening. Further, the extrusion die is so designed internally that the rate of flow is substantially even across the exit slot (lip) of the die. This is achieved by means of a carefully designed cavity that feeds the extrusion lip with material (See FIGS. 10 and 11). Preferably, this cavity is somewhat in the shape of a "coat hanger" and is an integral part of the extrusion die. The body of the extrusion die is heated to a few degrees Celsius (i.e., 2–10° C.), above the melting point of the film-forming composition. Unlike a spreader box, there is no reservoir of material and the ribbons are extruded under pressure.

Due to the ability of extrusion dies to produce films using pressurized film-forming material, the corresponding viscosities of the film-forming polymers may be significantly higher than the viscosity limits imposed by the prior art spreader box technology. Examples of films formed with viscosities at the casting temperature in the region of 80,000 to 120,000 cps have been produced.

FIG. 13 is a perspective view of a slightly different extrusion die from that shown in FIG. 3. The die according to FIG. 13, generally 130, comprises a film forming material entrance port 132, a back plate 134, and a front plate 136. The front plate 136 and the back plate 134 are attached to each other by numerous bolts 138. The ribbon to be extruded from the die is depicted as element 140. The extrusion slot 142 is an opening between the back plate 134 and the front plate 136. The inventors have discovered that the angle or pitch of the extruder head to the casting drum can be important to producing the best possible ribbon. For example, an extrusion die similar to that depicted in FIG. 13 is preferably placed at an angle of about 5° from perpendicular to the casting drum. See FIG. 13A.

Figure 13A:
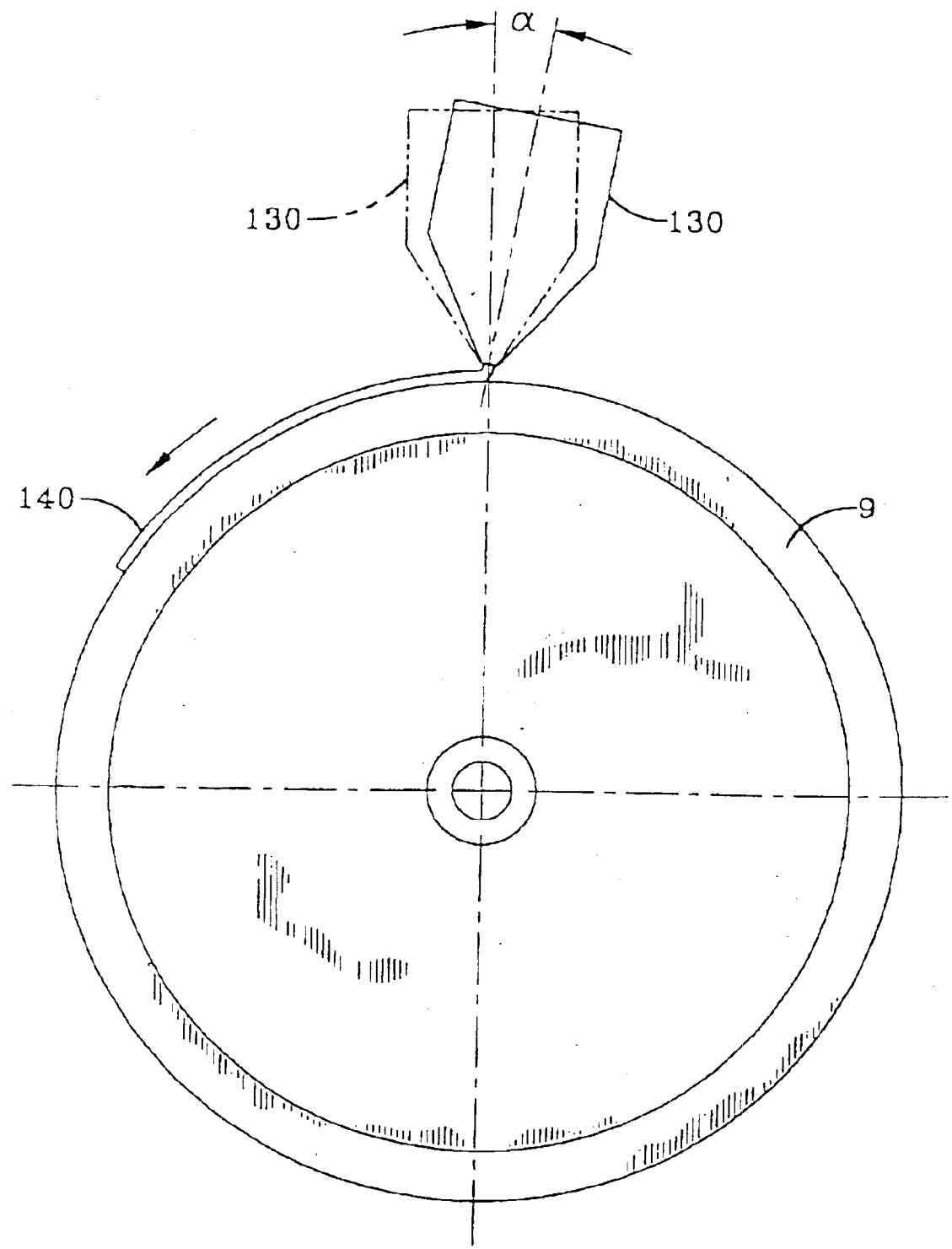
FIG. 13A is a side view of the casting drum and the tilted extrusion device.

FIG. 13A depicts a casting drum 9, the extrusion device 130 and the deposited film 140. The angle of a tilt-away from the flow of material can range from 2° to 10°; with 5° being preferred. Moving the extrusion die 130 from a perpendicular orientation improves the dimensional quality of the film 140 extruded from the exit slot of the die. If the die is mounted perpendicular to the casting drum surface, it can result in the formation of intermittent longitudinal lines or ridges, surface blemishes and general unevenness of the extruded film. Tilting the extrusion die typically 5° from perpendicular away from the direction of flow from the extrusion die has a dramatic effect on improving the quality and evenness of the films. The tilt is important, the degree of tilt can range from 2 to 10° from perpendicular depending on the characteristics of the film forming polymer and the desired film thickness.

The inventors have also found that the casting drum should be at about ambient temperature (i.e., 22–28° C.) as opposed to the conventional 10–12° C. In addition, it is preferred that air be blown on the casting drum at the rate of about 150–250 feet per minute (about 45–77 m/min.). This has been shown to increase the burst strength of the final capsules. These conditions are especially preferred when using the film forming composition disclosed in PCT/US00/18420 (supra).

Figure 9:
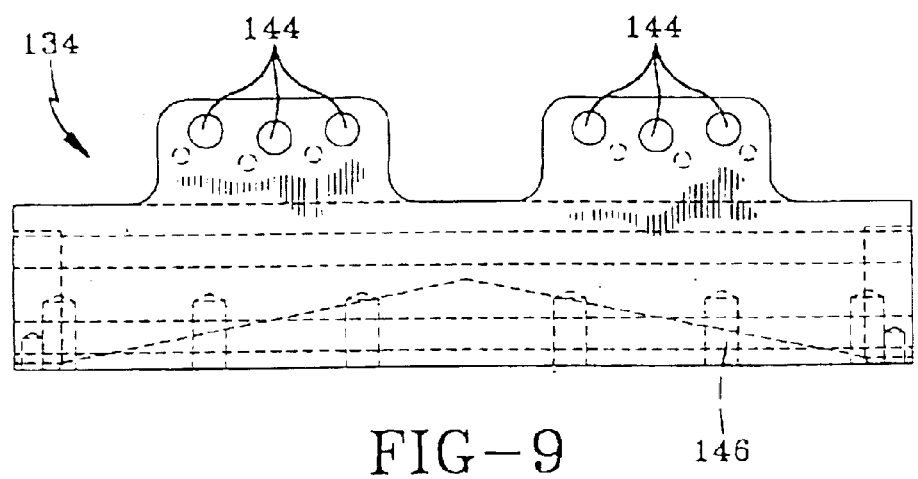
FIGS. 9–12 illustrate top (FIG. 9), side (FIG. 10) and end plan views (FIGS. 11 and 12) of the back plate of one embodiment of the sanitary, low pressure extrusion die.
Figure 10:
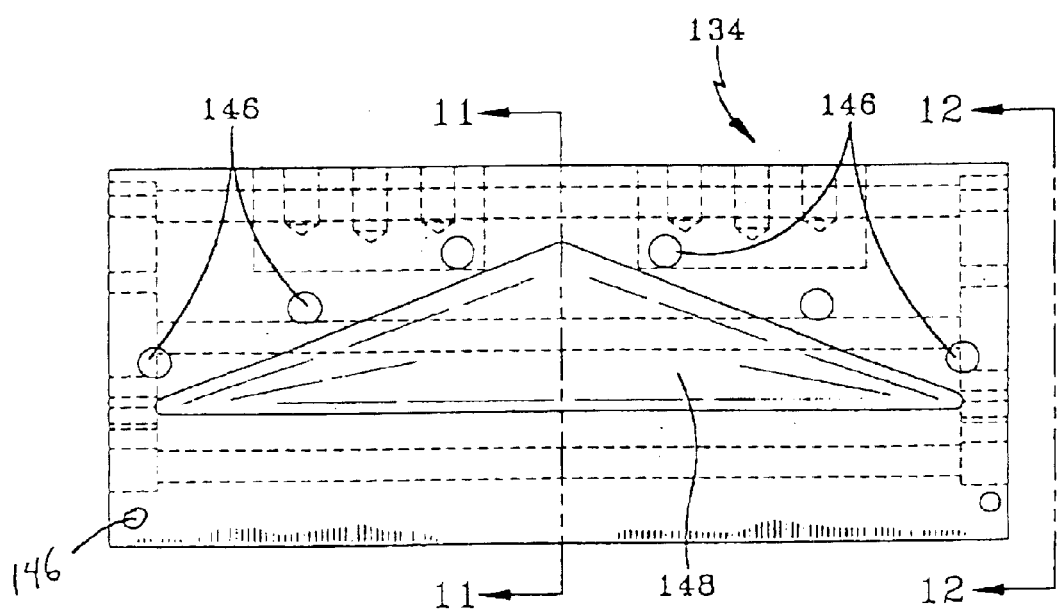

FIG. 9 is a top plan view of the back plate 134 of the extrusion die. Connecting bolt holes 144 are for attachment of the die to the encapsulation machine, while bolt holes 146 are for attachment of the front plate 136 to the back plate 134. FIG. 10 is a side view of the back plate showing the "coat-hanger" cavity 148 of the die.

Figure 11:
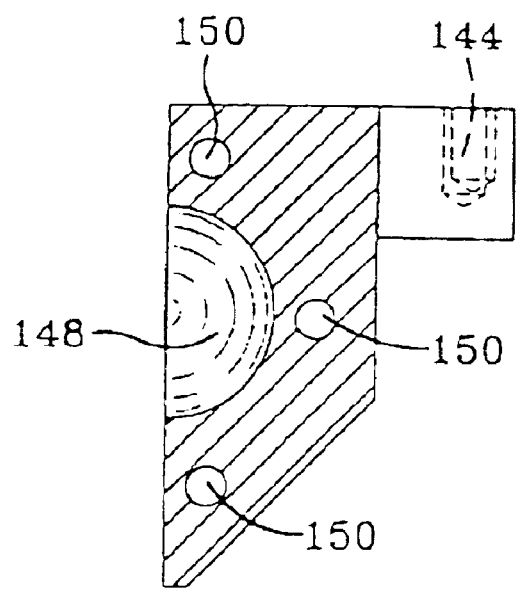
Figure 12:
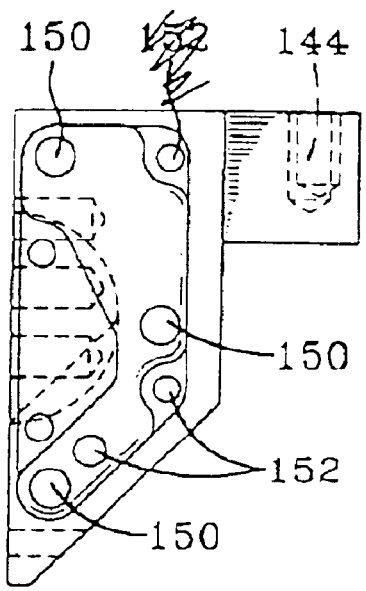

FIG. 11 is a cross section taken through FIG. 10 at line 11—11 showing the coat-hanger cavity 148 and cavities 150 for heating elements (not shown). FIG. 12 is a cross section taken through FIG. 10 at line 12—12 showing cavities 150 for the heating elements and thermisters 152 that are used to control the heating elements 150.

FIG. 14 is a top plan view of the front plate 136 illustrating the film-forming material entrance port 132 and numerous bolt holes 154. FIG. 15 is a side plan view of the front plate 136 of the extrusion device 130 illustrating the film forming material entrance port 132 and numerous bolt holes 154.

Figure 16:
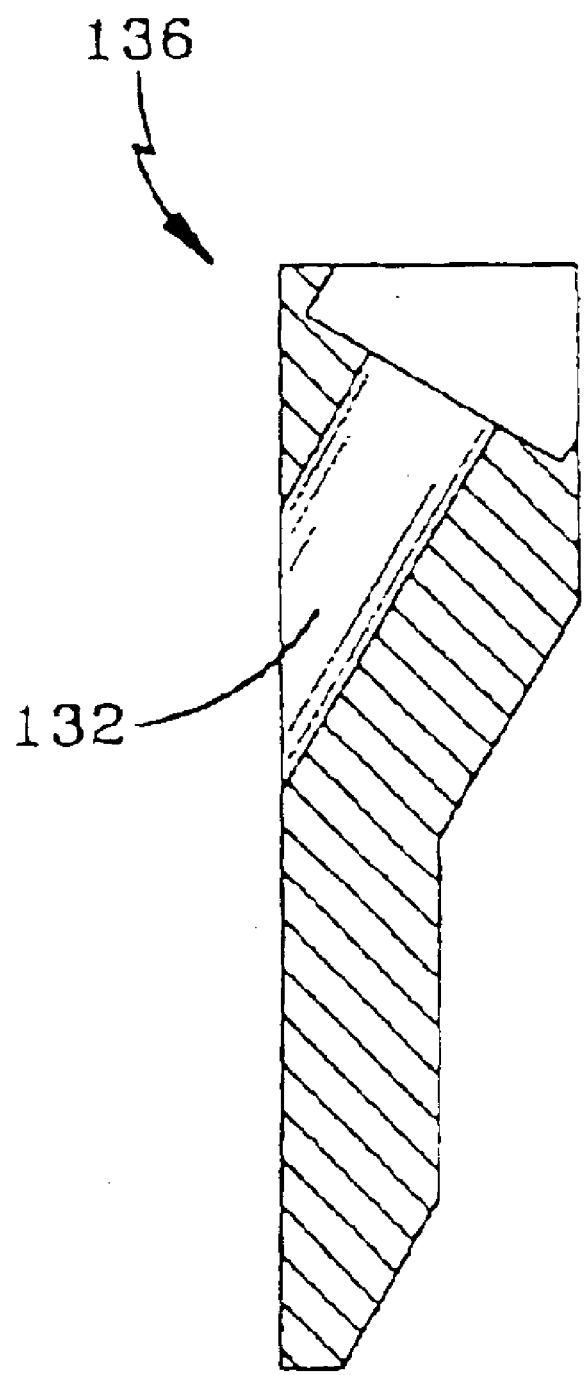
FIG. 16 is a cross section of the front plate taken through line 16—16 of FIG. 15.

FIG. 16 is a cross section of FIG. 15 taken through line 16—16 illustrating the film forming material entrance port 132.

Because the inventive system is an enclosed system, there are other advantages over the prior art spreader boxes. The open reservoirs of the spreader box are prone to water loss from the film-forming composition due to evaporation. In addition, the spreader box requires the additional complexity of a level feedback mechanism to control the filling of the spreader box chamber and prevent overflow. The extrusion dies of the present invention are in closed systems and can operate at higher temperatures if desired, without concerns for water loss. The inventive controlled and enclosed system exhibits better thermal control of the film-forming material being extruded. Further, extrusion dies overcome the inherent inaccuracies of spreader boxes which rarely produce geometrically even ribbons. It has been found that the extrusion dies according to the invention reduces the factors that cause variations in film thicknesses. It has been found that using the apparatus and process according to this invention, that the films produced are dimensionally more accurate and have considerably less dimensional variability than films produced using the prior art spreader boxes.

In addition, extrusion dies can be fabricated with a plurality of exit slots each individually fed with a different type of film-forming material. The slots can be mounted in series within a close proximity, i.e., within the same die body. Alternatively, the extrusion die can be so designed to accept a multitude of different feeds exiting into an internal die cavity/extrusion slot. In this way, the production of multilaminated ribbons can be enabled. Each laminate may have a separate composition and again, this offers further differentiation and versatility over the old spreader box technology.

A preferred type of pump for use in the inventive apparatus is a gear pump, however, other types of small lobe, helical worm, or piston pumps may suffice. The melt-on-demand devices should maintain the pumps at about the same temperature as the melt grid. The pump forces the flow of the film-forming material through heated tubes to the extrusion die. The speed of the pump determines the amount of material delivered to the extrusion die and hence, determines the thickness of the film extruded onto the casting drum.

INDUSTRIAL APPLICABILITY

The present inventive apparatus and process allows for the use of high viscosity film-forming systems for fabricating soft capsules. One limitation of the spreader box system of the prior art is the inability to produce ribbons or films from compositions that have viscosities in excess of 10,000 to 15,000 cps. Extrusion dies on the other hand, have been shown to easily handle 80 to 200,000 cps film-forming compositions.

One advantage of the inventive apparatus and process is the utilization of melt-on-demand technology as it overcomes the undesirable thermal degradation of the film-forming compositions. Gelatin is a typical polymer system used to manufacture soft capsules, however, using the current spreader box process requires the material to remain molten throughout use. Gelatin can only be kept in its molten state for 96 hours before sufficient degradation has occurred to render the system ineffective for making soft capsules. In contrast, the apparatus and process according to this invention heats the film-forming material only for 15 to 30 minutes prior to use. This is insufficient for undesirable degradation and loss of polymer function to occur. The apparatus and process according to the present invention provide a significant advance in the state of the art.

In the foregoing, there is provided a detailed description of preferred embodiments of the present invention for the purpose of illustration and not limitation. It is to be understood that all other modifications, ramifications and equivalents obvious to those having skill in the art based on this disclosure are intended to be within the scope of the invention as claimed.

We claim:

1. A film preparation apparatus comprising:
   a) at least one casting drum;
   b) means for melting solid film-forming material on demand;
   c) pump means; and
   d) an extrusion device;
   wherein said apparatus prepares encapsulation films from a solid film-forming material.

2. An apparatus according to claim 1 wherein said film-forming material has an aqueous component.

3. An apparatus according to claim 2 wherein said film-forming material comprises at least one component selected from the group consisting of starch, gelatin, carrageenans, gums and synthetic materials.

4. An apparatus according to claim 3 wherein said film-forming material comprises iota-carrageenan and modified starch; water a plasticizer, and a buffer.

5. An apparatus according to claim 3 wherein said film-forming material comprises gelatin, water and plasticizers.

6. An apparatus according to claim 1 wherein said means for melting solid said film-forming material comprises a melt grid.

7. An apparatus according to claim 8 wherein said melt grid is above the sold film-forming material.

8. An apparatus according to claim 6 wherein said melt grid is below said solid film-forming material.

9. An apparatus according to claim 1 wherein said pump means is a positive displacement pump.

10. An apparatus according to claim 9 wherein said positive displacement pump is selected from the group consisting of gear pumps, lobe pumps, sine pumps, worm pumps, and archimedes screws.

11. An apparatus according to claim 1 additionally comprising a reservoir means disposed between said means to melt said film-forming material and said extrusion device.

12. An apparatus according to claim 1 wherein said extrusion device comprises a chamber and an extrusion slot.

13. An apparatus according to claim 12 wherein said extrusion device is a coat hanger die.

14. An apparatus according to claim 11 additionally comprising a manifold disposed between said reservoir means and said extrusion device.

15. An apparatus for applying a polymer to a substrate comprising:
   a) means to melt a solid polymer on demand;
   b) pump means to transport the molten polymer to an extrusion device;
   c) reservoir means disposed between said means to melt said solid polymer and said extrusion device; and
   d) at least one casting drum.

16. The apparatus according to claim 1 wherein said extrusion device comprises a chamber and an extrusion slot.

17. The apparatus according to claim 16 wherein said extrusion device is a coat and hanger die.

18. The apparatus according to claim 15 additionally comprising a distribution manifold disposed between said reservoir means and said extrusion device.

* * * * *

UNITED STATES PATENT AND TRADEMARK OFFICE
CERTIFICATE OF CORRECTION

PATENT NO. : 6,884,060 B2  Page 1 of 1
APPLICATION NO. : 10/016352
DATED : April 26, 2005
INVENTOR(S) : Tanner et al.

It is certified that error appears in the above-identified patent and that said Letters Patent is hereby corrected as shown below:

Col. 14 lines 21-22 should read as follows:

7. An apparatus according to claim 8 wherein said melt grid is above the <u>solid</u> film-forming material.

Signed and Sealed this

Twenty-second Day of August, 2006

JON W. DUDAS
*Director of the United States Patent and Trademark Office*